(12) United States Patent
Ma

(10) Patent No.: US 7,151,120 B2
(45) Date of Patent: Dec. 19, 2006

(54) DEGRADABLE POROUS MATERIALS WITH HIGH SURFACE AREAS

(75) Inventor: Peter X. Ma, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 299 days.

(21) Appl. No.: 10/271,489

(22) Filed: Oct. 16, 2002

(65) Prior Publication Data

US 2003/0073158 A1 Apr. 17, 2003

Related U.S. Application Data

(60) Provisional application No. 60/330,205, filed on Oct. 17, 2001.

(51) Int. Cl.
*C08J 9/28* (2006.01)
*C08G 63/00* (2006.01)

(52) U.S. Cl. .......................... 521/64; 521/61; 521/182

(58) Field of Classification Search .................. 521/64, 521/182, 61
See application file for complete search history.

(56) References Cited

U.S. PATENT DOCUMENTS

| 5,541,234 A | 7/1996 | Unger et al. |
| 6,146,892 A | 11/2000 | Ma et al. |
| 6,281,257 B1 | 8/2001 | Ma et al. |

OTHER PUBLICATIONS

Young, T.H., L.P. Cheng, D.J. Lin, L. Fane, and W.Y. Chuang, *Mechanisms of PVDF membrane formation by immersion-precipitation in soft (1-octanol) and harsh (water) nonsolvents*, Polymer, 1999, vol. 40, No. 19: pp. 5315-5323.

Meier-Haack, J., W. Lenk, S. Berwald, T. Rieser, and K. Lunkwitz, *Influence of thermal treatment on the pervaporation separation properties of polyamide-6 membranes*, Separation and Purification Technology, 2000, vol. 19, No. 3: pp. 199-207.

Zhang, R. and P.X. Ma, *Synthetic nano-fibrillar extracellular matrices with predesigned macroporous architectures*, J Biomed Mater Res, 2000, vol. 52, No. 2: pp. 430-438.

Zhang, R. and P.X. Ma, *Processing of Polymer Scaffolds: Phase separation, Methods of Tissue Engineering*, Chapter 62, pp. 715-724, 2002, Academic Press.

Ma, P.X. and R. Zhang, *Synthetic nano-scale fibrous extracellular matrix*, J Biomed Mater Res, 1999, vol. 46, No. 1: pp. 60-72.

Zhu, S. and P.X. Ma, *Development of phase structure during the processing of poly(l-lactic acid) scaffolds for tissue engineering*, Polymer Preprints, 2000, vol. 41, No. 2: pp. 1675-1676.

Ruiyun, Z. and P.X. Ma, *Porous poly(L-lactic acid)/apatite composites created by biomimetic process*, J Biomed Mater Res, 1999, vol. 45: pp. 285-293.

Ruiyun, Z. and P.X. Ma, *Poly(α-hydroxyl acids)/hydroxyapatite porous composites for bone-tissue engineering. I. Preparation and morphology*, J Biomed Mater Res, 1999, vol. 44: pp. 446-455.

*Primary Examiner*—Irina S. Zemel
(74) *Attorney, Agent, or Firm*—Dierker and Associates, P.C.

(57) ABSTRACT

A method for preparing a highly porous, high surface area degradable or partially degradable material. The method comprises the steps of mixing a degradable or partially degradable polymer with a mixed solvent comprising a first solvent and a second solvent, wherein the mixed solvent comprises a ratio higher than 1:1, first solvent to second solvent; gelling the mixture; and treating the gel under conditions whereby a substantially solvent free porous structure is created having a porosity greater than about 80%; wherein the material is mechanically strong and has a complex porous structure with nano fibrous architecture.

14 Claims, 2 Drawing Sheets

DEGRADABLE POROUS MATERIALS WITH HIGH SURFACE AREAS

CROSS-REFERENCE TO RELATED APPLICATIONS

This application claims the benefit of U.S. Provisional Patent application Ser. No. 60/330,205, filed Oct. 17, 2001.

BACKGROUND OF THE INVENTION

The present invention relates generally to porous materials having high surface areas, and more particularly to such materials which are degradable or partially degradable, and methods for fabricating the same.

Membranes have been typically used for filtration (microfiltration, ultrafiltration, nanofiltration), reverse osmosis (hyperfiltration), dialysis, pervaporation, and gas separation applications. See, for example, Scott, K. and R. Hughes, *Industrial Membrane Separation Technology*, 1996, London: Blackie Academic & Professional; Baker, R. W., *Membrane technology and applications*, McGraw-Hill professional engineering, 2000, New York: McGraw-Hill; and Cardew, P. T., M. S. Le, and Royal Society of Chemistry, Process Technology Group, *Membrane processes: a technology guide*, 1998, Cambridge: Royal Society of Chemistry.

A solid membrane can be made of synthetic polymers, natural macromolecules, inorganic compounds, ceramic or metallic materials. These membrane materials are generally fabricated through sintering, stretching, extrusion, phase inversion and etching, or casting. See, for example, Scott, K. and R. Hughes, *Industrial Membrane Separation Technology*, 1996, London: Blackie Academic & Professional; and Pinnau, I. and B. D. Freeman, *Membrane formation and modification*, ACS symposium series, 744, 2000, Washington, D.C. [New York]: American Chemical Society, Distributed by Oxford University Press.

Porous membranes are advantageous in their low resistance to mass transfer of solutes in solution due to the increased permeation rate resulting from the pores. Therefore, porous membranes have been employed for separation of mixtures of proteins and macromolecules, salt concentration, sterilization, etc. They can also serve as 3-D matrices for chemical and biochemical mass exchange or reactions to take place, or for cells or other living organisms (e.g., bacteria, viruses, fungi) to grow. Therefore, they can be used as matrices in diagnostic systems, catalysis systems, culture systems, drug delivery systems, wound dressings, etc.

U.S. Pat. No. 6,146,892 discloses a method for producing nanofibrillar matrices utilizing degradable polymers, such as for example, poly(L-lactic acid) (PLLA), poly(D,L-lactic acid-co-glycolic acid) (PLGA), and the like. The disclosed nanofibrillar matrices are highly porous and work well for various applications. However, the pores sizes are very small (on the order of 2 $\mu$m to 3 $\mu$m), which may in some instances render it more difficult for cells to enter. Further, small pore sizes may render it more difficult for material transport, especially materials which are particulate or contain particles. Yet further, the disclosed non-fibrillar structure (a platelet structure) was not as mechanically strong as may be desirable in some instances.

SUMMARY OF THE INVENTION

The present invention comprises a method for preparing a highly porous, high surface area material, comprising the steps of mixing a degradable or partially degradable polymer with a mixed solvent comprising a first solvent and a second solvent, wherein the mixed solvent comprises a ratio higher than 1:1, first solvent to second solvent; gelling the mixture; and treating the gel under conditions whereby a substantially solvent free porous structure is created having a porosity greater than about 80%; wherein the material is mechanically strong and has a complex porous structure with nano fibrous architecture.

BRIEF DESCRIPTION OF THE DRAWINGS

Objects, features and advantages of the present invention will become apparent by reference to the following detailed description and drawings, in which.

DETAILED DESCRIPTION OF THE EMBODIMENTS

Figure 1A:
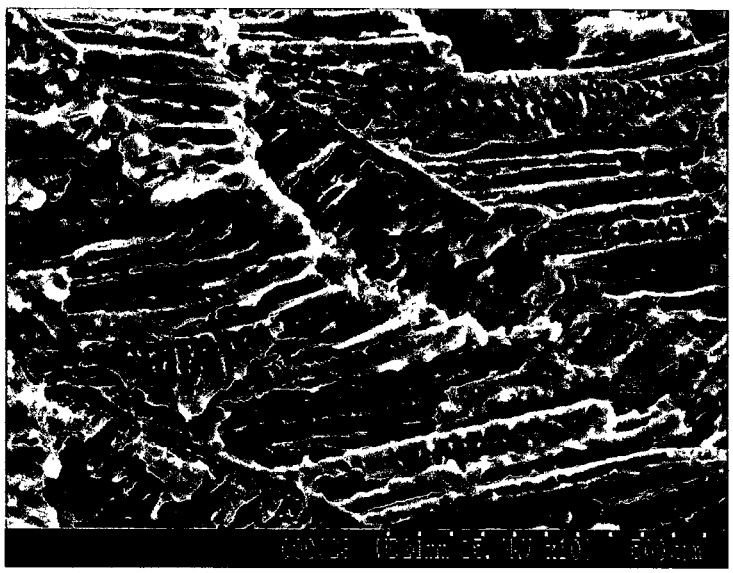
FIG. 1a is a SEM micrograph of porous PLLA material generated with PLLA solution in dioxane/pyridine mixed solvent with a ratio higher than 1:1, specifically, 7.5% PLLA in 2:1 dioxane/pyridine, at 100× magnification.

It would be desirable to provide highly porous structures having large pore sizes and high specific surface areas. It would further be desirable to provide such structures which are mechanically strong.

The present invention is predicated upon the unexpected and fortuitous discovery that a recently discovered phase separation technique may be utilized to render highly porous, mechanically strong, high surface areas materials having complex porous structure with nano fibrous architecture by using degradable or partially degradable polymers in a specific solvent system. The novel materials of the present invention may have pore sizes ranging between about 30 $\mu$m and about 300 $\mu$m, with similarly sized connections. In contrast, it had been expected that, whatever solvent/solvent system were used, if the process as disclosed in U.S. Pat. No. 6,146,892 were followed, it would render primarily relatively simple (non-complex), uniformly nanofibrous structures having relatively small pores (eg. pore sizes on the order of 2 $\mu$m to 3 $\mu$m).

High surface areas are very desirable in that, if a material has a very high surface area, less of the material (compared to a low surface area material) may be used in order to render the same result; ie. the reaction is more efficient.

Without being bound to any theory, it is believed that the ladder like structure contained within the nanofibrous structure of the present invention leads to the very high pore sizes disclosed herein. These large pore sizes promote and facilitate cell growth, mass transport processes, cell seeding, etc.

Some exemplary polymers suitable for the present invention comprise at least one of natural or synthetic hydrophilic polymers, natural or synthetic hydrophobic polymers, natural or synthetic amphiphilic polymers, degradable polymers, partially degradable polymers, and mixtures thereof.

Some polymers of choice are degradable polymers comprising at least one of poly(lactide-co-glycolide) (PLGA), poly(lactide) (PLA), poly(L-lactic acid) (PLLA), poly(D,L-lactic acid) (PDLLA), polyglycolic acid (PGA), polyanhydrides, poly(ortho ethers), and mixtures thereof.

Some exemplary, non-limitative degradable polymers (which may or may not be water soluble) include polyamino acids, engineered artificial proteins, natural proteins, biopolymers, and mixtures thereof.

Partially degradable polymers may be formed through the block copolymerization of a degradable polymer with a non-degradable polymer. Examples of non-degradable polymers include, but are not limited to the following:

Non-limitative water soluble (hydrophilic) non-degradable polymers include polyvinyl alcohol, polyethylene oxide, polymethacrylic acid (PMAA), polyacrylic acid, polyethylene glycol, alginate, collagen, gelatin, hyaluronic acid, and mixtures thereof. It is to be understood that the natural macromolecules such as alginate, collagen, gelatin and hyaluronic acid are generally not degradable unless treated with appropriate enzymes.

Non-limitative water insoluble (hydrophobic) non-degradable polymers include polytetrafluoroethylene (PTFE), polyvinylchloride (PVC), polyamides (PA, Nylons), polyethylenes (PE), polysulfones, polyethersulphone, polypropylenes (PP), silicon rubbers, polystyrenes, polycarbonates, polyesters, polyacrylonitrile (PAN), polyimides, polyetheretherketone (PEEK), polymethylmethacrylate (PMMA), polyvinylacetate (PVAc), polyphenylene oxide, cellulose and its derivatives, polypropylene oxide (PPO), polyvinylidene fluoride (PVDF), polybutylene, and mixtures thereof.

Some non-limitative examples of partially degradable polymers include a block copolymer of PMMA/PLA; and a block copolymer of polyethylene oxide/PLA.

It is to be understood that any suitable solvents may be used in the present invention, provided that the solvent(s) performs suitably within the context of the present inventive method. In an embodiment, a mixed solvent is used at a ratio of higher than 1:1, first solvent to second solvent. In an embodiment, the first solvent comprises dioxane, benzene, and mixtures thereof; and the second solvent comprises pyridine, tetrahydrofuran (THF), and mixtures thereof. It is to be understood that dioxane may be mixed with pyridine and/or THF; and that benzene may be mixed with pyridine and/or THF. In an embodiment, the ratio of first solvent to second solvent is 2:1; and in an alternate embodiment, the ratio of first solvent to second solvent is 3:1.

The dissolution/precipitation process is one of the most frequently used techniques to manufacture membrane materials. See, Young, T. H., L. P. Cheng, D. J. Lin, L. Fane, and W. Y. Chuang, *Mechanisms of PVDF membrane formation by immersion-precipitation in soft* (1-*octanol*) *and harsh* (*water*) *nonsolvents*, Polymer, 1999, 40(19): p. 5315–5323. In such technique, a polymer is first dissolved in a good solvent and cast on a substrate. The cast material is then immersed in a non-solvent or poor solvent for the polymer to induce polymer precipitation from the solution. Industrial membranes fabricated with such techniques have a specific surface area typically lower than 5 m$^2$/g (see Meier-Haack, J., W. Lenk, S. Berwald, T. Rieser, and K. Lunkwitz, *Influence of thermal treatment on the pervaporation separation properties of polyamide-6 membranes*, Separation and Purification Technology, 2000. 19(3): p. 199–207), and typically with an intermediate or low porosity (70% or lower).

The inventor of the present invention has recently developed a novel phase-separation technique to generate porous polymeric materials (porosity is typically higher than 80 or 90%) with a unique nano fibrous structure (an average fiber diameter ranging from 50 to 500 nm). See Ma, P. X. and R. Zhang, *Fibrillar Matrices*, in U.S. Pat. No. 6,146,892, 2000, which Patent is incorporated by reference herein in its entirety; Zhang, R. and P. X. Ma, *Synthetic nano-fibrillar extracellular matrices with predesigned macroporous architectures*, J Biomed Mater Res, 2000, 52(2): p. 430–438; and Zhang, R. and P. X. Ma, *Fabrication of polymer scaffolds: Phase separation*, in *Methods of Tissue Engineering*, A. Atala and R. Lanza, Editors, 2001, Academic Press: San Diego, Calif. (in press).

With the new techniques, dissolution/gelation (phase-separation)/solvent exchange (may be optional)/freezing/freeze-drying are some illustrative sequences to create the porous nano fibrous structure.

In contrast, as stated hereinabove, the present invention has unexpectedly and fortuitously discovered new complex porous (with greatly larger pore sizes than those of previous structures) structures with nano fibrous architecture (e.g., combined nano fibrous and ladder-like structures) and very high surface areas, which are fabricated with the new techniques. Their structures and properties generally depend on either the polymer/solvent systems and/or the phase-separation conditions; such as type of polymer(s), type of solvent(s), mixture ratio of two or more types of polymer(s) and/or solvent(s), polymer concentration, phase-separation temperature and so forth.

This invention discloses polymeric (or substantially polymeric) materials with very high surface areas, such as >5 m$^2$/g, >10 m$^2$/g, >20 m$^2$/g, >50 m$^2$/g, or much higher, and having porosity such as 70%80%, 90% or even higher, using the new fabrication techniques.

In an embodiment, the novel materials of the present invention have a specific surface area ranging between about 5 m$^2$/g and about 1000 m$^2$/g. In an alternate embodiment, the materials have a specific surface area ranging between about 10 m$^2$/g and about 500 m$^2$/g. In yet another alternate embodiment, the materials have a specific surface area ranging between about 20 m$^2$/g and about 200 m$^2$/g.

The novel materials of the present invention may have pore sizes ranging between about 30 µm and about 300 µm, with similarly sized connections. In an alternate embodiment, the novel materials of the present invention may have pore sizes ranging between about 50 µm and about 100 µm, with similarly sized connections.

The polymers may be synthetic or natural. They may be homopolymers (with one structural unit) or copolymers (with two or more structural units). The copolymers may be random copolymers, block copolymers, graft copolymers, and/or mixtures thereof. They may be one single polymer type or polymer blends. The materials may also be a composite of polymeric and non-polymeric materials. Further, it is to be understood that chemically or biologically active or inert materials may be involved as additives or as major components. These polymers may be physically, chemically, and/or biologically modified to improve certain properties or function. It is to be yet further understood that such modification may be carried out before fabrication (raw materials) or after fabrication of the porous materials.

Fabrication Techniques

1. Polymer Solution Preparation

Accurately weighed polymer(s) was added into a flask, and calculated amount of solvent(s) was added into the flask to make a polymer solution of a desired concentration. In an embodiment, the polymer solution (polymer/solvent mixture) contains between about 1% and about 20% polymer. Typically, the polymers were dissolved for two hours or longer to ensure a homogeneous solution when stirred with a magnetic stirrer at either room temperature or an elevated temperature (at or higher than room temperature, for example, 20° C., 40° C., 50° C., 60° C., 70° C. and so forth).

2. Porous Polymer Material Fabrication

Typically, four processing steps were taken to prepare a porous polymer material from a polymer solution: (A) Polymer solution (typically pre-warmed to a temperature at or higher than room temperature, for example, 20° C., 40° C., 50° C., 60° C., 70° C. and so forth) was added into a mold or container (e.g., Teflon vial). The mold containing the polymer solution was then rapidly transferred into a cooling device (e.g. a refrigerator or freezer) at a preset temperature to induce gelation. The cooling device is maintained at a predetermined temperature between about room temperature and about liquid nitrogen. The mold containing the polymer solution may be quenched in liquid nitrogen to induce gelation. The gelation time depended on temperature, solvent(s) and the polymer concentration of the solution. After gelation, the gel was kept at the gelling temperature for typically 2 hours or longer. (B) The mold containing the gel was immersed in a liquid (poor or non-solvent for the polymer) such as distilled water for solvent exchange. The water (or other liquid) was changed three times a day for two days. (C) The gel was removed from the water (or other liquid) and blotted by a piece of filter paper, and then was placed in a device set at a desired freezing temperature, the freezing temperature ranging between about room temperature and about liquid nitrogen. In an embodiment, the freezing temperature ranges between about room temperature and about −20° C. In an alternate embodiment, the freezing temperature ranges between about room temperature and about −70° C. The gel was frozen for typically 2 hours or longer. (D) The frozen gel was taken into a freeze-drying vessel, and was freeze-dried under a predetermined vacuum and at a predetermined temperature. It is to be understood that any suitable vacuum and temperature may be used; however, in an embodiment, a vacuum lower than 0.5 mmHg was used at a temperature ranging between about −5° C. and about −10° C. The frozen gel was freeze dried in an ice/salt bath for one week. The dried porous polymer material was then kept in a desiccator until characterization.

Characterization

The morphologies of the porous materials were examined with scanning electron microscopy (SEM) (S-3200N, Hitachi, Japan) at 15 kV. The samples were coated with gold using a sputter coater (Desk-II, Denton Vacuum Inc.) for 200 seconds with a gas pressure of lower than 50 mtorr and a current of about 40 mA.

The compressive mechanical properties of the scaffolds are measured with an MTS mechanical tester (Model: Synergie 200, MTS Systems Corporation, Cary, N.C.). Cubic specimens with a side length of 5 mm are compressed with a cross-head speed of 0.5 mm/min. The compressive modulus is determined from the initial linear region of the stress-strain curve, and the yield strength is determined from the cross point of the two tangents on the stress-strain curve around the yield point. At least six specimens are tested for each sample, and the averages and standard deviations are calculated.

To further illustrate the present invention, the following examples are given. It is to be understood that the examples are provided for illustrative purposes and are not to be construed as limiting the scope of the present invention.

EXAMPLES

1. PLLA in Dioxane and Pyridine:

PLLA was easily dissolved in a mixed solvent of dioxane and pyridine. We have previously found that PLLA solution could be used to fabricate nano fibrous PLLA foams with our fabrication techniques. See Ma, P. X. and R. Zhang, *Fibrillar Matrices*, in U.S. Pat. No. 6,146,892, 2000; Ma, P. X. and R. Zhang, *Synthetic nano-scale fibrous extracellular matrix*, J Biomed Mater Res, 1999, 46(1): p. 60–72; and Zhu, S. and P. X. Ma, *Development of phase structure during the processing of poly (l-lactic acid) scaffolds for tissue engineering*, Polymer Preprints, 2000, 41(2): p. 1675–1676.

Figure 1B:
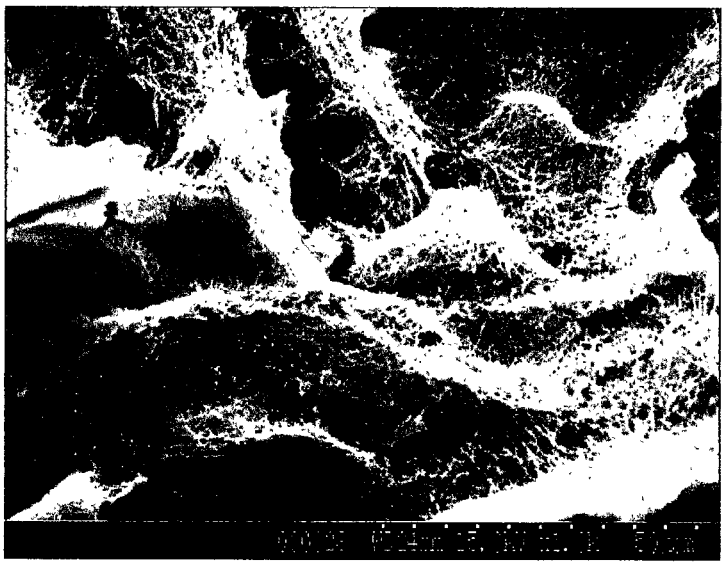
FIG. 1b is a SEM micrograph of porous PLLA material generated with PLLA solution in dioxane/pyridine mixed solvent with a ratio higher than 1:1, specifically, 7.5% PLLA in 2:1 dioxane/pyridine, at 1000× magnification.
Figure 1C:
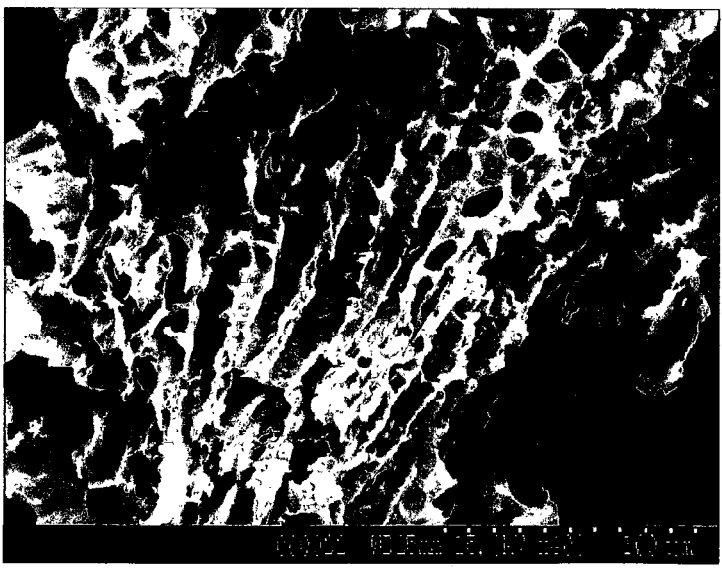
FIG. 1c is a SEM micrograph of porous PLLA material generated with PLLA solution in dioxane/pyridine mixed solvent with a ratio higher than 1:1, specifically, 7.5% PLLA in 3:1 dioxane/pyridine, at 400× magnification.
Figure 1D:
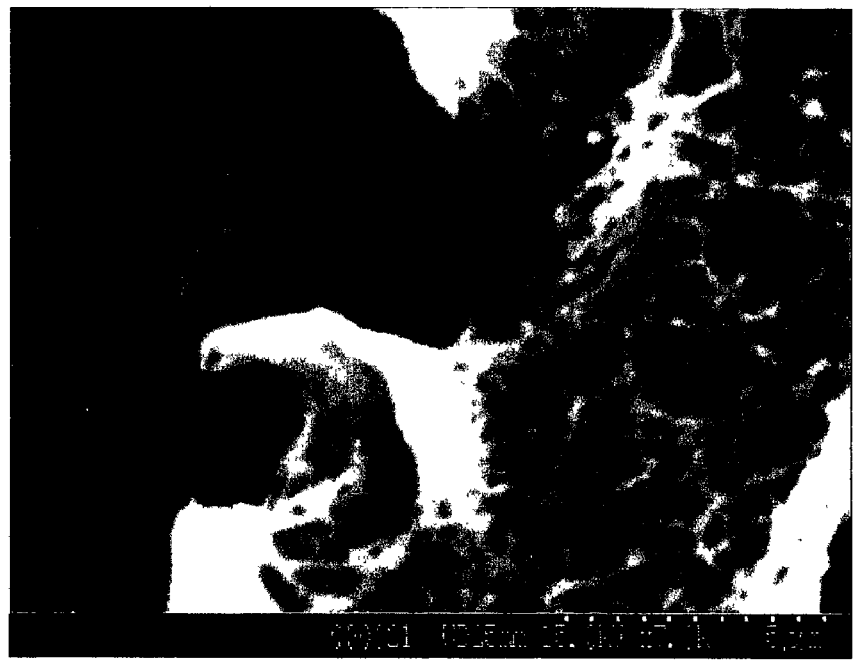
FIG. 1d is a SEM micrograph of porous PLLA material generated with PLLA solution in dioxane/pyridine mixed solvent with a ratio higher than 1:1, specifically, 7.5% PLLA in 3:1 dioxane/pyridine, at 7000× magnification.

However, in the present invention, it has been unexpectedly and fortuitously found that if the solvent is a mixture of dioxane and pyridine with a ratio of dioxane/pyridine higher than 1:1, certain complex architectures can be generated with such techniques. In embodiments of the present invention, ratios of 2:1 and 3:1 dioxane to pyridine were used. However, it is to be understood that any ratio higher than 1:1 may be used to gain the advantages of the present invention. Some typical complex morphologies, e.g. porous architecture at the micrometer scale (such as ladder-like) and fibrous architecture at the nanometer scale, are shown in FIGS. 1a–1d.

2. PLGA in Benzene and THF:

PLGA is dissolved in a mixed solvent of benzene and THF. Ratios of 2:1 and 3:1 benzene to THF are used. The polymer/solvent mixture contains between about 1% and about 20% PLGA. However, it is to be understood that any ratio higher than 1:1 may be used to gain the advantages of the present invention. The porous materials have complex morphologies, e.g. porous architecture at the micrometer scale (such as ladder-like) and fibrous architecture at the nanometer scale.

Mechanical Properties and Specific Surface Area:

In the examples of the present invention described above, the inventive highly porous materials have interesting architectural features, which are novel. They have high potential to be used in a variety of biomedical, industrial and household applications. For many of these applications, a high specific surface area and the mechanical integrity are important.

The porous materials generated in the present invention are believed to have excellent mechanical properties and higher specific surface areas than previously known porous materials.

As disclosed herein, the present invention comprises non-degradable porous materials having very high surface areas, and methods for fabricating the same. A variety of 3D architectures with features at the nanometer and/or micrometer scales may advantageously be generated. The materials may be synthetic polymers, natural macromolecules, or their derivatives. They may be hydrophilic, hydrophobic, or amphiphilic. Further, the materials may be homopolymers, co-polymers, blends, mixtures, or composites of polymers. The novel porous materials may advantageously be used in a variety of applications including medical devices (eg. artificial kidney, dialysers), matrix materials for chemical reactors, bioreactors, controlled release devices, wound dressings, separation membranes, filters, catalysis systems, absorbents, packaging and insulating materials. Further, the porous materials may be desirable for use as tissue engineering scaffolds for a variety of applications, including implants.

While preferred embodiments, forms and arrangements of parts of the invention have been described in detail, it will be apparent to those skilled in the art that the disclosed embodiments may be modified. Therefore, the description herein is to be considered exemplary rather than limiting, and the true scope of the invention is that defined in the following claims.

What is claimed is:

1. A porous material, comprising:
   at least one degradable or partially degradable polymer; and
   pores having a size and connections therebetween, wherein the pore sizes range between about 30 μm and about 300 μm, and wherein the connections range in size between about 30 μm and about 300 μm, wherein the porous material porosity is greater than about 80%;
   wherein the porous material has a high specific surface area ranging between about 10 m$^2$/g, and about 1000 m$^2$/g, and has a random architecture formed from one phase-separation process, the random architecture including porous architecture at the micrometer scale and fibrous architecture at the nanometer scale.

2. The porous material as defined in claim 1 wherein the at least one degradable or partially degradable polymer comprises at least one of natural or synthetic hydrophilic polymers, natural or synthetic hydrophobic polymers, natural or synthetic amphiphilic polymers, and mixtures thereof.

3. The porous material as defined in claim 2 wherein the at least one degradable or partially degradable polymer is a degradable polymer comprising at least one of poly(lactide-co-glycolide) (PLGA), poly(lactide) (PLA), poly(L-lactic acid) (PLLA), poly(D,L-lactic acid) (PDLLA), polyglycolic acid (PGA), polyanhydrides, poly(ortho ethers), and mixtures thereof.

4. The porous material as defined in claim 2 wherein the at least one degradable or partially degradable polymer is a degradable polymer comprising at least one of polyamino acids, engineered artificial proteins, natural proteins, biopolymers, and mixtures thereof.

5. The porous material as defined in claim 2 wherein the at least one degradable or partially degradable polymer is a partially degradable polymer comprising at least one degradable polymer block copolymerized with at least one non-degradable polymer selected from a hydrophilic non-degradable polymer or a hydrophobic non-degradable polymer;
   wherein the hydropbilic non-degradable polymer includes at least one of polyvinyl alcohol, polyethylene oxide, polymethacrylic acid (PMAA), polyacrylic acid, polyethylene glycol, alginate, collagen, gelatin, hyaluronic acid, or mixtures thereof; and
   wherein the hydrophobic non-degradable polymer includes at least one of polytetrafluoroethylene (PTFE), polyvinylchloride (PVC), polyamides (PA, Nylons), polyethylenes (PE), polysulfones, polyethersulphone, polypropylenes (PP), silicon rubbers, polystyrenes, polycarbonates, polyesters, polyacrylonitrile (PAN), polyimides, polyetheretherketone (PEEK), polymethylimethacrylate (PMMA), polyvinylacetate (PVAc), polyphenylene oxide, cellulose and its derivatives, polypropylene oxide (PPO), polyvinylidene fluoride (PVDF), polybutylene, or mixtures thereof.

6. The porous material as defined in claim 5 wherein the at least one degradable polymer, forming a portion of the partially degradable polymer, includes at least one of poly(lactide-co-glycolide) (PLGA), poly(lactide) (PLA), poly(L-lactic acid) (PLLA), poly(D,L-lactic acid) (PDLLA), polyglycolic acid (PGA), polyanhydrides, poly(ortho ethers), polyamino acids, engineered artificial proteins, natural proteins, biopolymers, or mixtures thereof.

7. The porous material as defined in claim 6 wherein the partially degradable polymer comprises a block copolymer of PMMA and PLA.

8. The porous material as defined in claim 6 wherein the partially degradable polymer comprises a block copolymer of polyethylene oxide and PLA.

9. The porous material as defined in claim 1 wherein the porosity is greater than approximately 85%.

10. The porous material as defined in claim 9, wherein the porosity is greater than approximately 90%.

11. The porous material as defined in claim 10, wherein the porosity is approximately 98%.

12. The porous material as defined in claim 1 wherein the porous material has a specific surface area ranging between about 10 m$^2$/g and about 500 m$^2$/g.

13. The porous material as defined in claim 12 wherein the porous material has a specific surface area ranging between about 20 m$^2$/g and about 200 m$^2$/g.

14. The porous material as defined in claim 1 wherein the pore sizes range between about 50 μm and about 100 μm, and wherein the connections range in size between about 50 μm and about 100 μm.

* * * * *